United States Patent [19]

Smith

[11] Patent Number: 4,916,314

[45] Date of Patent: Apr. 10, 1990

[54] METHOD AND APPARATUS FOR ANALYZING COMPONENTS OF SELECTED FLUID INCLUSIONS

[75] Inventor: Michael P. Smith, Tulsa, Okla.

[73] Assignee: Amoco Corporation, Chicago, Ill.

[21] Appl. No.: 248,526

[22] Filed: Sep. 23, 1988

[51] Int. Cl.⁴ .............................................. H01J 37/26
[52] U.S. Cl. .................................... 250/307; 250/310; 250/399; 250/442.1
[58] Field of Search ............ 250/310, 306, 307, 442.1, 250/399

[56] References Cited

U.S. PATENT DOCUMENTS

| | | |
|---|---|---|
| 3,761,709 | 9/1973 | Hasegawa et al. ................ 250/441.1 |
| 4,117,323 | 9/1978 | Greer et al. .......................... 250/311 |
| 4,149,803 | 4/1979 | Litz ........................................ 356/36 |
| 4,331,872 | 5/1982 | Soga et al. ........................... 250/399 |
| 4,749,868 | 6/1988 | Hatanaka et al. ................. 250/442.1 |

OTHER PUBLICATIONS

"Cryogenic Scanning Electron Microscope of Fluids Inclusions in Ore and Gangue Minerals", Kelley et al., Economic Geology, vol. 78 1983, pp. 1262–1267.

Primary Examiner—Bruce C. Anderson

[57] ABSTRACT

Nonvolatile componets of targeted fluid inclusions in mineral specimens are analyzed by exposing the fluid inclusion using ion-abrason and then analyzing the exposed inclusion using an electron microprobe.

17 Claims, 4 Drawing Sheets

METHOD AND APPARATUS FOR ANALYZING COMPONENTS OF SELECTED FLUID INCLUSIONS

FIELD OF THE INVENTION

The invention relates to method and apparatus for analyzing fluid inclusions and more particularly to such method and apparatus in which a fluid inclusion formed in a material such as mineral, glass, semiconducting material and the like is uncovered and the contents therein, including nonvolatiles, are analyzed to determine atomic element(s) present.

SETTING OF THE INVENTION

Fluid inclusions in minerals may be formed at the time of mineral growth or they may form later when cracks in the minerals heal. Fluid inclusions formed at the time of initial mineral growth are referred to as primary inclusions and those formed during healing of cracks in the already-formed mineral are referred to as secondary inclusions. Cracks which have formed and healed at different times in the mineral's past produce different generations of secondary inclusions which trap environmental fluids present at the time of healing of the crack. Sometimes a mineral overgrowth which acts as a cement may form between and around previously-formed mineral growths. Environmental fluids may also be trapped in fluid inclusions formed in the cement. Fluid inclusions in sedimentary rocks are less than 100 microns, typically less than 10 microns along their major diameter.

Fluid inclusions may be ruptured to release the volatile paleofluids contained therein to analyze them. Such analysis can be used to determine information relating to the nature of the fluids present when the mineral was formed. This information is useful in the exploration for and production of oil and gas. For example, such studies can produce information relating to timing of hydrocarbon migration relative to rock formation, pathways of hydrocarbon migration, and the influence of hydrocarbons on rock formation.

The analysis of the nonvolatile components contained in fluid inclusions presents a problem. Such components are typically not released upon rupturing of the inclusion and therefore some special technique for analysis of specifically the nonvolatile components is required. Preferably such technique should be applicable to selected individual fluid inclusions.

The nonvolatile components present in environmental fluids are of particular importance because these nonvolatile components determine the nature of the brines responsible for creating and destroying porosity and permeability in the rock. The results of such studies can be used to predict the likely course of migration of brines creating or destroying porosity, the resulting porosity and the likely path of movement of hydrocarbons. Previously, paleobrine compositions have been inferred from petrographic examination of the rock. Thus, porosity type has been used to infer brine composition but not vice versa.

Method and apparatus are needed for analysis of the nonvolatile brine components of fluid inclusions to permit development of correlations for predicting porosity type from brine composition.

Further, knowledge of paleobrine composition is important in evaluating the direction of hydrocarbon migration. Thus, for example, using sophisticated techniques, it is possible to determine hydrocarbon (particularly methane) content of fluid inclusions. It is not possible, however, without knowledge of the brine to determine the degree of methane saturation in such inclusions. Such information is needed to provide information concerning directions of possible migration of hydrocarbons.

SUMMARY OF THE INVENTION

According to the invention, there is provided method and apparatus for analyzing the composition of nonvolatile components of specific individually selected fluid inclusions.

The invention comprises method and apparatus for determining atomic elements in a fluid inclusion in a matrix. A matrix-abrading ion beam is directed at matrix adjacent overlaying the inclusion uncovering the inclusion. Then, an X-ray emission stimulating beam of electrons is directed at the uncovered inclusion simulating emission of characteristic X-rays. The atomic element(s) present in the uncovered inclusion are determined from the intensities of their characteristic X-rays.

In a further aspect, the invention comprises drawing a vacuum on a chamber containing a specimen of matrix having fluid inclusion(s) therein and then freezing the inclusion(s) in the specimen. The step of drawing a vacuum is effective for reducing condensation of condensibles in the chamber during freezing. Thereafter, a matrix-abrading ion beam is directed at matrix adjacent overlaying a selected frozen target inclusion in the specimen and the frozen target inclusion is exposed. Then an X-ray emission stimulating beam of electrons is directed at the exposed frozen target inclusion stimulating emission of characteristic X-rays therefrom. The emitted characteristic X-rays are then analyzed to determine atomic elements present in the frozen target inclusion.

DETAILED DESCRIPTION OF THE INVENTION

Figure 1:
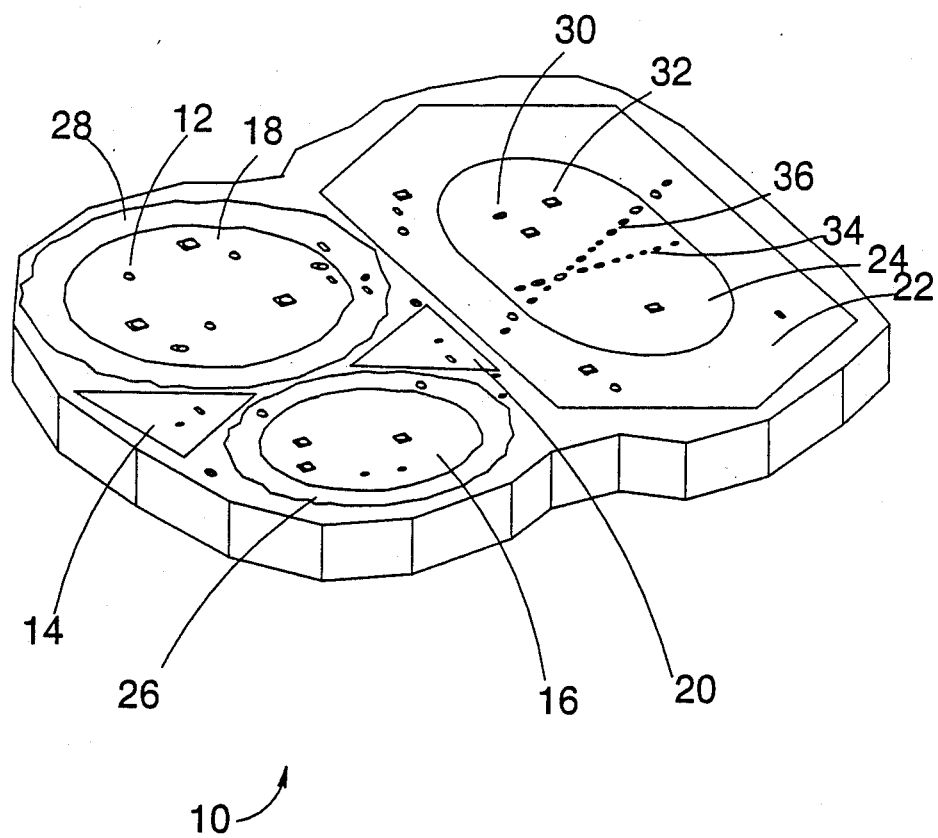
FIG. 1 illustrates fluid inclusions as viewed in a thin mineral section.

Turning now to the drawings and particularly to FIG. 1, consideration will be given to an example of a mineral sample containing a plurality of mineral growths. Indicated generally at 10 is a portion of a sample extracted from naturally-occurring mineral growth. Sample 10 consists of a cut section having a thickness of approximately 0.03–1.0 mm which is polished on both sides and which can be mounted on a glass slide. The view of FIG. 1 is a view of the polished section as seen through the microscope and is thus greatly enlarged. The approximate scale can be indicated in that substantially all of the fluid inclusions, like inclusion 12, formed in the various mineral growths in sample 10 are under 10 microns in diameter. Sample 10 includes a plurality of mineral growths, like minerals 14, 16, 18, 20, 22, and 24. Minerals 16 and 18 each include a mineral overgrowth 26 and 28 which acts as and is referred to herein as a cement.

Mineral 24 includes therein a plurality of primary inclusions like inclusion 30, 32. These inclusions were formed during the initial growth of mineral 24. A healed crack 34 is formed in mineral 24 and a healed crack 36 is formed in mineral 22 and in mineral 24. Crack 34 was formed in mineral 24 after the original growth of mineral 24, and thus after the primary inclusions, like inclusion 30, 32, were formed. Cracks 34, 36 were also formed in minerals 22, 24 after the formation of the primary inclusions in mineral 32. Each of cracks 34, 36 have a plurality of secondary inclusions as shown. The secondary inclusions were formed during healing of cracks 34, 36 when mineral growth developed in the cracks. It is to be appreciated that the secondary inclusions in crack 34 trap environmental fluids at a later time than the primary inclusions in mineral 24, and the secondary inclusions along crack 36 trap such fluids at a later time than when the environmental fluids were trapped in the primary inclusions in both minerals 22, 24. Moreover, the secondary inclusions in crack 34 may well be formed at a time far removed from those formed in crack 36 and thus the secondary inclusions in crack 34 may be of a different generation than those along crack 36. Likewise, the primary inclusions formed in the various minerals and cements in sample 10 may be formed at vastly different times from one another, thus trapping the environmental fluids present at the time of formation.

It should be noted that sample 10 may be taken from a portion of naturally-occurring mineral growth using the usual sawing and polishing techniques. After the sample is cut, polished and mounted on a slide, the same may be observed through a microscope to obtain the view of FIG. 1. Geologists are able to identify by observation through the microscope various types of minerals. Such petrographic analysis is based on well known criteria of shape of mineral growth and various optical properties. In addition, the fluid inclusions themselves can be classified in different ways such as the above-described primary and secondary fluid inclusions. Other categories of inclusions classifications may be utilized; however, most common is classifying by origin, namely, primary and secondary inclusions. Such inclusions may be characterized by observation of the sample through the microscope.

Figure 2:
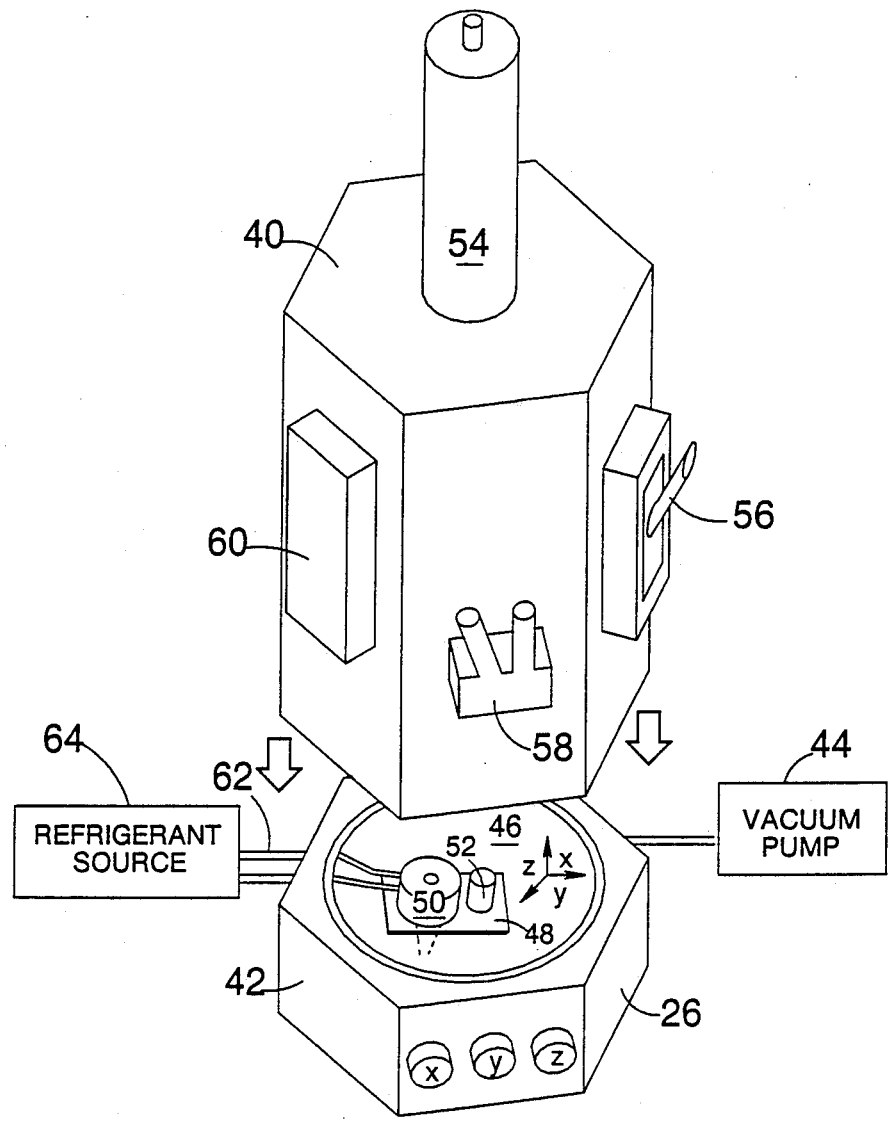
FIG. 2 illustrates apparatus in accordance with the invention.

Turning now to FIG. 2 in detail, according to the invention there is provided apparatus for analysis of nonvolatile components of fluid inclusions in a mineral sample on a microscale.

The apparatus has a housing 40 and 42. Upper housing 40 and lower housing 42 can be evacuably engaged so that vacuum pump 44 can evacuate the chamber 46 formed within the combined housing.

The chamber 46 in lower housing 42 receives a sample stage 48 having a refrigeratible sample holder 50 and a reference sample holder 52. The sample stage 48 can be positioned as desired in a three-dimensional target area in the chamber as illustrated by motion arrows in cavity 46 and by controllers X, Y, Z on the front of the lower housing 42.

The upper housing 40 has an electron gun 54 and an ion gun 56 for impinging on a selected target zone on a sample held by sample holders 50 or 52. Preferably, the electron gun 54 and the ion gun 56 are mounted to housing 40 so that both can impinge, without changing position controls X, Y, and Z, on a target area of a mineral specimen. For example, the electron gun can be positioned to impinge vertically on a target area and the ion gun can be directed at an angle, for example 52.5° from vertical to impinge on the same target area. The target area can be selected using microscope 58 and position controls X, Y, Z.

Upper housing 40 also has, for example, energy dispersive spectrometers 60 mounted thereon for sensing characteristic X-rays emitted from an inclusion when electron-stimulated. Wavelength spectrometers might also be used; however, energy-dispersive spectrometers require fewer electrons to impinge on the target to produce effective signals for detection.

The apparatus illustrated in FIG. 2 can be readily constructed from a conventional electron microprobe equipped with energy-dispersive spectrometers such as DELTA SYSTEM® available from KEVEX, INC. One of the spectrometers can be replaced with an ion gun such as available from Perkin-Elmer Corporation on a mounting assembly which can be readily constructed for the purpose.

The sample stage 48 likewise can be readily constructed from the description herein. At least one of the sample holders 50 is refrigeratible. This can be used by using a temperature-conductive support, such as brass, equipped with cooling means such as coil 62 through which a refrigerant such as a suitable Freon or liquid nitrogen passes. The cooling coils pass through the evacuable housing 42 to a refrigerant source 64 as shown.

Figure 3:
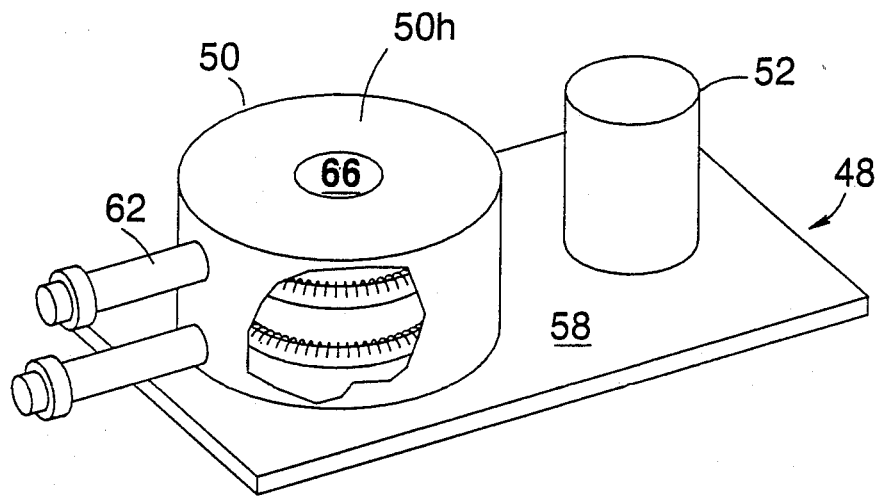
FIG. 3 illustrates a sample holder stage in accordance with the invention.

The sample holder 48 is shown in more detail in FIG. 3. As illustrated, the refrigeratible sample holder 50 can comprise a generally cylindrical brass housing 50H having cooling coils 62 in contact with the inside wall. The upper end of the housing 50H has a window 66 therein above which a specimen can be placed and which permits illumination from below for convenient viewing of the specimen by microscope 58 (see FIG. 2) during positioning. Sample holder 52 can be similarly constructed or can be as shown without adaptation for refrigeration. Both holders 50 and 52 can be mounted on a common structure 58 which can be adapted for the positioning stage of a electron microprobe as is known.

Figure 4:
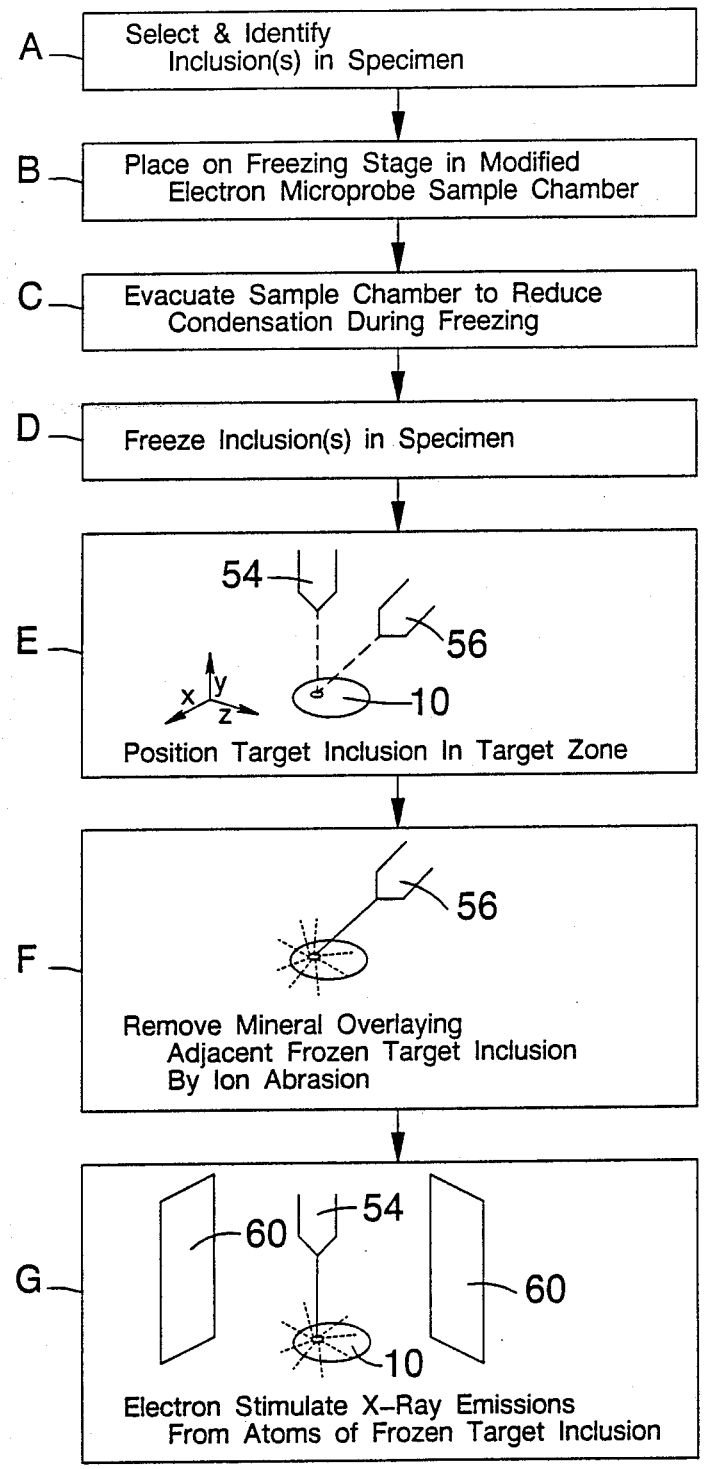
FIG. 4 illustrates schematically method in accordance with the invention.

Referring now to FIG. 4, the invented method is schematically illustrated. A mineral specimen is placed in the viewing stage of an optical microscope and petrographic analysis conducted as is known. According to the invention, one or more fluid inclusions are selected and marked for analysis. While marking is not required for practicing the invention, it permits use of the invented apparatus shown in FIGS. 2 and 3 without time lost in searching for inclusions. This step is illustrated as A of FIG. 4.

The mineral specimen is then placed on the refrigeratible holder of the sample stage 48, optionally a reference sample is placed on the reference holder 52, and the loaded stage 48 is placed within the electron microprobe sample chamber 46. This step is illustrated by B in FIG. 4.

A vacuum seal is effected on the modified electron microprobe in the usual way and the sample chamber 46 is evacuated, for example, to $10^{-6}$ torr or less to prevent condensation of condensibles present in the chamber 46 during later freezing of the specimen. This step is illustrated by C in FIG. 4.

After evacuation, the sample is frozen by circulating coolant such as liquid nitrogen from source 64 through cooling coil 62 to the refrigeratible holder 50 within the chamber. This step is illustrated as D in FIG. 4.

After or concurrently with evacuation and freezing, a selected inclusion can be positioned in a target zone for the ion gun 56 using position controls X, Y, Z. Preferably, as indicated, the target zone for ion gun 56 and electron gun 54 is the same. This step is illustrated by E in FIG. 4.

The ion gun is activated to direct a beam of ions to the target zone to remove minerals overlaying adjacent the selected inclusion. This process can be monitored using the microscope 58 of the modified electron microprobe. This step is illustrated by F in FIG. 4.

The electron gun is then activated and electron stimulates atomic elements contained in the target inclusion to emit characteristic X-rays. The emitted X-rays are detected by energy-dispersive spectrometer 60, a wavelength spectrometer (not shown), or the like and interpreted to identify atomic elements contained in the inclusion. The interpretation of energy dispersive spectrometer data is well known. This step is illustrated by G in FIG. 4.

The invented apparatus and method can be used to analyze and identify nonvolatile components in inclusions. Such nonvolatile atoms in aqueous inclusions include magnesium, calcium, sodium, potassium, chlorine, sulfur, iron, barium, strontium, and the like. In hydrocarbon inclusions, such nonvolatile atoms can include carbon, nitrogen, oxygen, sulfur, nickel, vanadium, and in general atoms other than hydrogen.

The analyses of the non-volatile components of individual fluid inclusions may allow the prediction of nearby dolomitization. Dolomitizing fluids typically have high Mg/Ca ratios. Documentation of fluid inclusions with this characteristic in a sandstone would suggest that nearby limestone may be dolomitized.

On the other hand, fluids that have dolomitized limestone already are typically Ca-chloride rich. Documentation of Ca-chloride fluid inclusions in limestone would suggest nearby dolomitization.

Most production of oil and gas from carbonates in North America is from dolomite and not limestone. This is usually attributed to enhanced porosity and greater strength. In some areas, hydrocarbon exploration is essentially dolomite exploration, i.e. if you find dolomite you find production.

Thus in accordance with the invention is a method for exploring for dolomites by analysis of nonvolatile components of fluid inclusions. A mineral specimen, preferably a thin prepared mineral section, is provided from a region under investigation. After petrographic analysis, selected fluid inclusions are uncovered and nonvolatile components analyzed by the invention and the calcium and magnesium content of the included brines are determined.

In limestone, for example, the presence of calcium rich brine is an indicator of dolomitization of nearby limestone, i.e., upstream (relative to the direction of paleo fluid flow) from the formation under study.

In sandstone, for example, the presence of fluids rich in magnesium is an indication of the presence of potentially dolomitizing fluid, the likely absence of dolomite in the upstream direction (i.e., the direction from which the fluid flowed) and the potential presence of dolomite in downstream limestones (i.e., limestones occurring downstream of the sandstone in the direction of the brine flow. Conversely, the presence of calcium brines in sandstone is an indicator that dolomitization is more likely upstream than downstream of the sandstone.

As indicated, the invented method evacuates the sample chamber before the sample is frozen. As a result, condensation of atmospheric water is prevented without the necessity of excluding water from the ambient air during sample preparation and analysis.

As indicated, covering minerals are removed adjacent overlaying selected inclusions after freezing by ion sputtering or abrasion. As a result, specific targeted target inclusions can be sampled rather than such inclusions as might randomly be exposed, for example, by splitting frozen host material.

The invented apparatus and method provide for understanding diagenesis by analysis of nonvolatile components of selected inclusions on a microscale.

The invention also provides for direct analysis of brines responsible for creating or destroying porosity in sedimentary rock. On the microscale of interest in the present invention, such information has previously had to be inferred from rock geochemical analyses. By providing direct knowledge of brine contents, the invention facilitates modeling the processes which form the rock, created and destroyed porosity, and the like for evaluating whether porosity was present when hydrocarbons might have been formed or flowed though the rock, the direction of flow of brines, and of hydrocarbons, and the like.

In oil and gas exploration, fluid inclusions are potentially of great significance in making interpretations of the subsurface rock/fluid interactions that control reservoir quality and quantity. They are important because they represent miniature samples of the subsurface brines that are and have been interacting with the rocks. The most characteristic feature of these brines is the chemistry of the dissolved solids. The various elements present provide information about the origin and history of the brines, and how they have interacted with the rocks.

It will be appreciated that there has been provided apparatus and method of the highest significance to analysis of oil and gas reservoirs, and which heretofore have not been available to oil and gas explorationists. By use of the invention, degree of hydrocarbon saturation in microscopic fluid inclusions can be analyzed taking into consideration the brine composition of the inclusion fluid. Further, indicators of direction of nearby or potential or lack of dolomitization can also be produced. Other uses and advantages will be apparent to those skilled in reservoir analysis.

While the invention has been described in terms of particular embodiments to facilitate understanding, the invention is not limited to those embodiments but by the claims appended hereto interpreted in accordance with applicable principles of law.

What is claimed is:

1. Method for obtaining information useful in exploring for oil and gas by analyzing composition of nonvolatile components of specific individually targeted fluid inclusions in sedimentary mineral matrix comprising:

in a sample chamber of an electron microprobe, directing a matrix-abrading ion beam at matrix adjacent overlaying a specific individually targeted fluid inclusion in a specimen of sedimentary mineral matrix comprising a plurality of fluid inclusions less than 100 microns in diameter;

uncovering and exposing specifically the individually targeted fluid inclusion;

then, using the electron microprobe, directing an X-ray emission stimulating beam of electrons at the specific individually targeted uncovered and exposed inclusion stimulating emission of characteristic X-rays and determining atomic elements present in the uncovered and exposed inclusion from the emitted characteristic X-rays.

2. The method of claim 1 comprising:
drawing a vacuum on the sample chamber of the electron microprobe containing the specimen of sedimentary mineral matrix having a plurality of fluid inclusions therein;
freezing the inclusions in the specimen while in the chamber under vacuum;
the step of drawing a vacuum being effective for reducing condensation of condensibles in the chamber during freezing;
in the sample chamber of the electron microprobe, directing a matrix-abrading ion beam at matrix adjacent overlaying the specific individually targeted frozen fluid inclusion in the specimen uncovering and exposing the specific individually targeted frozen fluid inclusion;
directing an X-ray emission stimulating beam of electrons at the uncovered and exposed frozen targeted inclusion stimulating emission of characteristic X-rays; and
determining atomic elements present in the uncovered frozen target inclusion from the emitted characteristic X-rays.

3. The method of claim 2 wherein:
the steps of directing beams at a targeted inclusion include a step of positioning a targeted inclusion in a target zone for each beam.

4. The method of claim 3 wherein:
the step of positioning includes using a microscope for positioning the targeted inclusion in the target zone for each beam.

5. The method of claim 2 wherein:
inclusions to be targeted are identified and selected using a microscope prior to the specimen being placed in the chamber;
the method comprising placing the specimen on a specimen holder and the specimen holder in the chamber;
evacuating the chamber to prevent condensation of condensibles in the chamber during freezing;
freezing the specimen in the evacuated chamber;
directing a matrix abrading ion beam at matrix adjacent overlaying a specific individually targeted frozen fluid inclusion in the specimen;
uncovering and exposing the frozen fluid inclusion;
directing an X-ray emission stimulating beam of electrons at the uncovered and exposed frozen target inclusion stimulating emission of characteristic X-rays;
determining atomic elements present in the uncovered and exposed frozen target inclusion from the emitted characteristic X-rays using an energy dispersant spectrometer.

6. The method of claim 5 further comprising:
providing a specimen holder stage having at least one refrigeratible specimen holder;
placing the specimen on the refrigeratible specimen holder;
placing the specimen holder stage in the chamber; and
freezing the specimen by circulating coolant through the refrigeratible specimen holder.

7. The method of claim 1 comprising:
providing a mineral specimen taken from a reservoir;
providing measures of nonvolatile atomic elements in specific individually targeted and analyzed fluid inclusions as indicators of oil or gas in or adjacent the reservoir.

8. The method of claim 7 comprising determining one of magnesium and calcium in fluid inclusions in a mineral specimen.

9. The method of claim 8 comprising determining magnesium and calcium in fluid inclusions in the mineral specimen.

10. The method of claim 9 comprising:
indicating the direction and occurrence of dolomitization in a reservoir from thus determined magnesium and calcium.

11. An electron microprobe for determining atomic elements in a fluid inclusion in a matrix comprising:
a sample chamber for receiving a specimen of sedimentary mineral matrix comprising a plurality of fluid inclusions;
means in the sample chamber for directing a matrix-abrading ion beam at matrix adjacent overlaying a specific individually targeted fluid inclusion in the specimen for uncovering and exposing the specific targeted inclusion;
means in the sample chamber for directing an X-ray emission stimulating beam of electrons at the uncovered and exposed individually targeted fluid inclusion stimulating emission of characteristic X-rays and means for determining atomic elements present in the uncovered inclusion from the emitted characteristic X-rays.

12. The electron microprobe of claim 11 further comprising:
a housing defining the sample chamber for receiving the specimen;
means for drawing a vacuum on the sample chamber having received a specimen of matrix having fluid inclusion(s) therein;
means for freezing inclusion(s) in the specimen in the sample chamber;
means for directing a matrix abrading ion beam at matrix adjacent overlaying a frozen individually targeted fluid inclusion in the specimen exposing the frozen specific targeted inclusion;
means for directing an X-ray emission stimulating beam of electrons at the uncovered frozen specific targeted inclusion stimulating emission of characteristic X-rays; and
means for analyzing the emitted characteristic X-rays and determining atomic elements present in the specific frozen targeted inclusion.

13. The electron microprobe of claim 12 wherein
the housing defining the sample chamber includes a sample stage positioning means for positioning a sample stage in a target zone for the ion beam and the electron beam, the ion beam and the electron beam both impingable on a targeted inclusion in the target zone without changing position of the sample stage positioning means; and further comprising:
a sample stage comprising at least one refrigeratible sample holder, the sample holder being refrigerated by passing cooling fluid in contact therewith, while the sample stage is in the chamber and the chamber is evacuated.

14. The electron microprobe of claim 13 wherein the sample stage comprises:

a light transmitting support for a specimen;

means in thermally conductive contact with the support for cooling the support and a supported specimen; and means for passing cooling fluid in contact with the means for cooling.

15. The electron microprobe of claim 13 wherein the sample stage comprises:

a sample holder;

cooling means in heat transfer communication with the sample holder for freezing fluids in a sample placed on the sample holder;

the sample holder being position-controlled by the sample stage positioning means of the microprobe; and the cooling means being effective for freezing the sample after the sample chamber of the electron microprobe is evacuated.

16. The electron microprobe of claim 15 comprising:

means in flow communication between a refrigerant source and the cooling means for circulating refrigerant fluid therebetween.

17. The Apparatus of claim 11 wherein the means for directing a matrix abrading ion beam and the means for directing an X-ray emission stimulating beam of electrons are mounted in the electron microprobe so that both beams are impingable on a targeted inclusion in the specimen without changing position of the specimen.

* * * * *